United States Patent
Kohnle et al.

(10) Patent No.: US 8,967,493 B2
(45) Date of Patent: Mar. 3, 2015

(54) ATOMIZING DEVICE

(75) Inventors: Joerg Kohnle, VS-Schwenningen (DE);
Frank Keppner, Albstadt (DE);
Hubertus Pfeffer, Schwackenreute (DE)

(73) Assignee: Aptar Radolfzell GmbH, Radolfzell (DE)

( * ) Notice: Subject to any disclaimer, the term of this patent is extended or adjusted under 35 U.S.C. 154(b) by 876 days.

(21) Appl. No.: 13/134,371

(22) Filed: Jun. 6, 2011

(65) Prior Publication Data

US 2011/0303761 A1    Dec. 15, 2011

(30) Foreign Application Priority Data

Jun. 15, 2010 (DE) .......................... 10 2010 024 913

(51) Int. Cl.
| | |
|---|---|
| *B05B 1/08* | (2006.01) |
| *A61M 15/00* | (2006.01) |
| *A61M 11/00* | (2006.01) |
| *B05B 17/06* | (2006.01) |
| *B05B 17/00* | (2006.01) |

(52) U.S. Cl.
CPC ......... *A61M 15/0085* (2013.01); *A61M 11/005* (2013.01); *B05B 17/0607* (2013.01); *B05B 17/0638* (2013.01); *A61M 15/0065* (2013.01); *A61M 2205/21* (2013.01); *A61M 2205/7536* (2013.01); *A61M 2205/8206* (2013.01)
USPC .......................... 239/102.1; 239/124; 239/127

(58) Field of Classification Search
USPC .............................. 239/102.1, 102.2, 124, 127
See application file for complete search history.

(56) References Cited

U.S. PATENT DOCUMENTS

| | | |
|---|---|---|
| 5,164,740 A | 11/1992 | Ivri |
| 5,586,550 A | 12/1996 | Ivri et al. |
| 5,758,637 A | 6/1998 | Ivri et al. |
| 5,938,117 A | 8/1999 | Ivri |
| 6,014,970 A | 1/2000 | Ivri et al. |
| 6,085,740 A | 7/2000 | Ivri et al. |
| 6,205,999 B1 | 3/2001 | Ivri et al. |
| 6,427,682 B1 | 8/2002 | Klimowicz et al. |

(Continued)

FOREIGN PATENT DOCUMENTS

| | | |
|---|---|---|
| DE | 696 33 122 T2 | 7/2005 |
| DE | 10 2004 006 452 A1 | 8/2005 |

(Continued)

OTHER PUBLICATIONS

Examination Report issued in the German Patent Office dated Mar. 10, 2011 (3 pages).

(Continued)

*Primary Examiner* — Jason Boeckmann
(74) *Attorney, Agent, or Firm* — Flynn, Thiel, Boutell & Tanis, P.C.

(57) ABSTRACT

An atomizer for atomizing liquids including a liquid storage receptacle pertaining to an atomizing device having an atomizing chamber that communicates with the ambient atmosphere through a plurality of outlet orifices. A vibrator is also provided, which liquid present in the atomizing chamber is caused to vibrate for the purpose of atomization, and an intake channel is provided, via which the liquid storage receptacle is connected to the atomizing device and a pumping device is also provided in the intake channel for the purpose of conveying the liquid from the liquid storage receptacle to the atomizing chamber, An electronic control device controls the pumping device and the vibrator.

12 Claims, 3 Drawing Sheets

(56) References Cited

U.S. PATENT DOCUMENTS

| | | |
|---|---|---|
| 6,467,476 B1 | 10/2002 | Ivri et al. |
| 6,540,153 B1 | 4/2003 | Ivri |
| 6,581,852 B2 | 6/2003 | Garcia et al. |
| 6,629,646 B1 | 10/2003 | Ivri |
| 6,640,804 B2 | 11/2003 | Ivri et al. |
| 6,755,189 B2 | 6/2004 | Ivri et al. |
| 6,782,886 B2 | 8/2004 | Narayan et al. |
| 6,814,071 B2 | 11/2004 | Klimowicz et al. |
| 6,921,020 B2 | 7/2005 | Ivri |
| 6,926,208 B2 | 8/2005 | Ivri |
| 7,040,549 B2 | 5/2006 | Ivri et al. |
| 7,083,112 B2 | 8/2006 | Ivri |
| 7,108,197 B2 | 9/2006 | Ivri |
| 7,174,888 B2 | 2/2007 | Ivri et al. |
| 7,584,903 B2 | 9/2009 | Koerner et al. |
| 7,628,339 B2 | 12/2009 | Ivri et al. |
| 7,770,757 B2 * | 8/2010 | Helmlinger ............ 222/189.11 |
| 7,815,924 B2 | 10/2010 | Vonbehren et al. |
| 7,832,658 B2 * | 11/2010 | Kaneko et al. ............ 239/102.2 |
| 7,837,129 B2 | 11/2010 | Schuerle et al. |
| 2002/0011247 A1 | 1/2002 | Ivri et al. |
| 2002/0023639 A1 | 2/2002 | Ivri et al. |
| 2002/0070239 A1 | 6/2002 | Garcia et al. |
| 2002/0104530 A1 | 8/2002 | Ivri et al. |
| 2002/0121274 A1 | 9/2002 | Borland et al. |
| 2002/0185125 A1 | 12/2002 | Klimowicz et al. |
| 2003/0000520 A1 | 1/2003 | Ivri et al. |
| 2003/0019493 A1 | 1/2003 | Narayan et al. |
| 2003/0226906 A1 | 12/2003 | Ivri |
| 2004/0000598 A1 | 1/2004 | Ivri |
| 2004/0004133 A1 | 1/2004 | Ivri et al. |
| 2004/0139963 A1 | 7/2004 | Ivri et al. |
| 2005/0201870 A1 | 9/2005 | Koerner et al. |
| 2005/0207917 A1 | 9/2005 | Koerner et al. |
| 2005/0263608 A1 | 12/2005 | Ivri |
| 2005/0279851 A1 | 12/2005 | Ivri |
| 2006/0115438 A1 | 6/2006 | Vonbehren et al. |
| 2006/0255174 A1 | 11/2006 | Ivri et al. |
| 2007/0075161 A1 | 4/2007 | Ivri |
| 2007/0209659 A1 | 9/2007 | Ivri et al. |
| 2009/0236437 A1 | 9/2009 | Schuerle et al. |
| 2010/0071687 A1 | 3/2010 | Hsieh et al. |

FOREIGN PATENT DOCUMENTS

| | | |
|---|---|---|
| DE | 10 2004 011 726 A1 | 9/2005 |
| DE | 601 20 614 T2 | 5/2007 |
| DE | 10 2006 061 506 A1 | 6/2008 |
| JP | 60-54761 A | 3/1985 |
| JP | 61-97066 A | 5/1986 |
| JP | 61-35912 B2 | 8/1986 |
| JP | 1-166767 A | 6/1989 |
| JP | 2005-246377 A | 9/2005 |
| JP | 2006-503061 A | 1/2006 |
| JP | 2006-116448 A | 5/2006 |

OTHER PUBLICATIONS

European Patent Office Search Report issued in Application No. EP 11 16 6167.4 dated Jun. 1, 2012 with English translation of categories of cited documents (14 pages).

Office Action from EPO issued in Application No. EP 11 166 167.4 dated Feb. 25, 2014 (7 pages).

English translation of Office Action of Japan Patent Office issued in Application No. 2011-126311 dated Sep. 25, 2014 (4 pages).

\* cited by examiner

ATOMIZING DEVICE

FIELD OF APPLICATION AND PRIOR ART

This application claims the priority of the German patent application No. 10 2010 024 913.0. The whole disclosure of this prior application is herewith incorporated by reference into this application.

The invention relates to an atomizer for atomizing liquids, more particularly pharmaceutical or cosmetic liquids. A generic atomizer comprises a liquid storage receptacle and an atomizing device comprising an atomizing chamber that communicates with the ambient atmosphere by means of a plurality of outlet orifices, and a vibrator, by means of which liquid present in the atomizing chamber can be caused to vibrate for the purpose of atomization. Furthermore, a generic atomizer comprises an intake channel, by means of which the liquid storage receptacle is connected to the atomizing device, and a pumping device that is provided in the intake channel for the purpose of conveying liquid from the liquid storage receptacle to the atomizing chamber. An electronic control device is provided for controlling the pumping device and the vibrator.

Generic atomizers are known in the prior art. They are used for atomizing liquids to a fine spray. These liquids are, in particular, pharmaceutical or cosmetic liquids. In the case of pharmaceutical liquids, the purpose of atomization can consist, for example, in the production of a very readily inhalable spray by means of the atomizer. In the case of cosmetic liquids, the purpose of atomization can consist in achieving a very homogeneous discharge by means of the atomizer, for example for the production of a very homogeneous layer of liquid on an area of the skin.

The pumping device of generic atomizers can serve the purpose of providing a continuous supply of liquid to the atomizing device. However, it has been found that it is difficult to coordinate the pumping device and the atomizing device in such a way that the pumped volumetric flow rate produced by the pumping device perfectly matches the rate of atomization of the liquid. In the case of an extremely high pumped volumetric flow rate, there is the risk of deterioration of the atomizing characteristics in that the liquid flows through the discharge orifices in a non-atomized state and covers the side of the discharge orifices remote from the atomizing device with a liquid film to obstruct atomization. In the case of an extremely low pumped volumetric flow rate, it is likewise impossible to achieve good quality atomization, since comparatively large amounts of air gather in the atomization chamber and counteract the discharge of liquid in an atomized form. These disadvantages are particularly problematic in an atomizer that is intended for use in different positions. This positional variability can be desirable for various reasons. Thus, for example, in an atomizer used for the inhalation of medicines, it is desirable that the atomizer be usable by the patient in different positions, for example, in a standing or lying position. In the case of an atomizer used for cosmetic products that are to be applied to different areas of the skin, it is difficult to do this when the atomizer is held in a constantly invariable position. The variable orientation of a generic atomizer intensifies the aforementioned problem since it can promote the entry of air into the atomizing chamber. In addition, pressure conditions in the atomizing chamber depend to a major extent on the orientation and movement of the atomizer.

In order to deal with the problem of achieving coordination between the pumping device and the atomizing device, it is known in the prior art, for example from DE 10 2004 006 452 A1, to activate the pumping device and the vibrator successively. Initially, the atomizing chamber itself and any capillary channel directly connected thereto are filled with liquid by means of the pumping device. Then the vibrator is activated in order to discharge the amount of liquid introduced into the atomizing chamber and the capillary channel. The disadvantage of such a design is that the amount of liquid discharged is small. It is thus impossible to achieve a continuous atomizing process. This is a considerable disadvantage in the case of some medicines and also in the case of cosmetic liquids.

OBJECT AND ITS ACHIEVEMENT

It is an object of the invention to develop a generic atomizer by achieving a continuous atomizing process whilst avoiding considerable effort in achieving coordination between the pumping device and the atomizing device. More particularly, it is desired to provide an atomizer that is suitable for use in an atomizing process in which it can be held at different orientations.

According to the invention, this object is achieved by the provision of a return channel, which is distinct from the intake channel and serves to drain liquid from the atomizing chamber into the liquid storage receptacle. Thus a channel leading from the atomizing chamber to the liquid storage receptacle is provided in such a design in addition to the intake channel through which the liquid is conveyed by the pumping device from the liquid storage receptacle to the atomizing chamber of the atomizing device. It is the primary task of this return channel to recirculate excess liquid from the atomizing chamber to the liquid storage receptacle. This allows the atomizing chamber to be fed at a volumetric flow rate of liquid that is significantly greater than the discharged volumetric flow rate as can be atomized by means of the atomizing device. The excess amount of liquid is not discharged through the outlet orifices, but instead it flows through the return channel back into the liquid storage receptacle. The return channel can be dimensioned appropriately for this purpose. This structure ensures continuous atomization of liquid, during which sufficient liquid is always available for the purpose of atomization in that a volumetric flow rate of liquid that is clearly greater than the atomized volumetric flow rate is fed continuously to the atomizing chamber. Furthermore, even if air enters the atomizing chamber through the outlet orifices, the return channel enables this air to be removed from the atomizing chamber and to flow together with the excess liquid into the liquid storage receptacle. Thus the atomizer of the invention ensures a very reproducible and constant atomizing process.

The atomizing device of an atomizer of the invention is similar to atomizing devices known in the prior art. The liquid present in the atomizing chamber is caused to vibrate by the vibrator, which is preferably in the form of a piezoelectric vibrator, such that a reproducible discharge of liquid through the plurality of very small outlet orifices is achieved under substantially constant pressure conditions in the atomizing chamber. The liquid discharged is replaced, by means of the pumping device, with liquid from the liquid storage receptacle. For this purpose, the pumping device is preferably in the form of a micropump. Such a micropump can have, for example, a pump chamber which is provided with an inlet valve and an outlet valve and which is cyclically enlarged and reduced in volume by means of one or more piezoelectric actuators.

For the purpose of achieving a homogeneous discharging behavior, the pumped volumetric flow rate of the liquid fed by the pumping device to the atomizing chamber is greater than the discharged volumetric flow rate of liquid passing through the outlet orifices. The discharged volumetric flow rate depends significantly on the design of the atomizing device and on the activation of the vibrator by means of the control device. The pumped volumetric flow rate depends on the design of the pumping device itself and its activation by the control device and the design of the channels conveying the liquid. The desired pumped volumetric flow rate that is greater than the discharged volumetric flow rate can be achieved by means of an appropriate design of the atomizing device, the pumping device, and the channels, and particularly by means of the activation thereof by the control device.

It is of particular advantage when the pumped volumetric flow rate is greater than the discharged volumetric flow rate by at least 20% during the atomizing process. It is more advantageous when the pumped volumetric flow rate is greater than the discharged volumetric flow rate to an even greater extent. It is even more advantageous when the pumped volumetric flow rate is greater than the discharged volumetric flow rate by 40% or more. The homogeneity of the atomizing process is ensured very effectively when the amount of liquid delivered by the pumping device is significantly greater than the amount of liquid atomized by the atomizing device.

In principle, it is feasible for the control device to be configured so as to start the pumping device and the vibrator simultaneously in response to a start signal, for example in response to actuation by a user. However, it is regarded as being advantageous when the control device is configured so as to activate the pumping device first in a preparatory phase before the atomizing process commences and to additionally activate the vibrator on termination of the preparatory phase. The preparatory phase, which preferably lasts at least 0.3 seconds and more preferably at least 0.8 seconds, ensures that the atomizing chamber is completely filled with liquid prior to activation of the vibrator and that a positive pressure ensues in the atomizing chamber due to the activity of the device. These are ideal set-up conditions for subsequent activation of the vibrator and thus for triggering the atomizing process.

Particularly to prevent liquid from being discharged through the outlet orifices of the atomizing device under the pressure generated by the pumping device during the preparatory phase, it is advantageous for the pumping device to be configured and/or to be activated by the control device and for the outlet orifices of the atomizing device to be configured such that the pressure ensuing in the atomizing chamber in the preparatory phase is not sufficient to force the liquid through the outlet orifices. This can be achieved by the use of small outlet orifices, by selecting a suitable shape of the outlet orifices, and/or by establishing a low pressure in the atomizing chamber. The pressure must be adjusted such that it suffices only in combination with the vibrations produced by the vibrator to force the liquid through the outlet orifices. A comparatively low pressure can be produced in the atomizing chamber by means of appropriate adjustment of the pumping device. However, a throttle that is distinct from the pumping device is advantageous for this purpose.

Basically any form of liquid reservoir can be used as the liquid storage receptacle. In the simplest case, the liquid storage receptacle can be, for example, a dimensionally stable liquid reservoir, into which a riser pipe connected to the pumping device extends. Particularly with regard to the functional efficiency of the atomizer in various orientations, it is considered to be advantageous when the liquid storage receptacle is in the form of a dimensionally flexible liquid-containing bladder that can adapt itself in terms of its internal volume to the amount of liquid present therein. Such a dimensionally flexible liquid-containing bladder does not require any aeration since, irrespective of the remaining volume, the pressure of the liquid in the liquid-containing bladder does not vary significantly, but instead is always equal to the ambient pressure. Such a liquid storage receptacle is filled exclusively with liquid except for the gaseous residues mentioned below, so that the pumping device will always draw in liquid. In the case of the present invention, the liquid storage receptacle has two openings, one of which is connected to the intake channel and the other to the return channel. The use of a liquid-containing bladder is additionally advantageous due to the very low risk of contamination associated therewith.

It is advantageous to provide a debubbling device since, inter alia, even the use of such a liquid-containing bladder cannot completely exclude the possibility of gas entering the liquid-containing bladder when the latter is being filled with liquid and the further possibility of air that has passed through the outlet orifices into the atomizing chamber of likewise entering the liquid storage receptacle by way of the return channel. The debubbling device is preferably provided in the intake channel and more preferably between the pumping device and the atomizing chamber.

This debubbling device ensures that the liquid fed to the atomizing chamber is free from gas bubbles, at least to a significant extent. Positioning of the debubbling device between the pumping device and the atomizing chamber additionally assists the removal of gas bubbles from the liquid in the debubbling device due to the pressure produced on the pump output side. Preferably, the debubbling device comprises a duct, through which the liquid flows on its way to the atomizing chamber and which is delimited, in part, by a filter surface. This filter surface allows the gas to escape at the pressure produced by the pumping device, while the pressure on the output side of the pump is not sufficient to force the liquid through the filter surface. Preferably, the filter surface is hydrophobic, in order to reduce contact with the liquid as far as possible, so that any gas bubbles will be adsorbed on the filter surface.

In a particularly advantageous design of the debubbling device, the aforementioned duct is formed by a groove that is located in a base component and is closed by the flat porous filter surface applied to this base component. This is a structurally very simple solution. The base component can be preferably provided in the form of a plastics component, in which the groove is formed during manufacture of the component, through which groove the liquid will flow on its way to the atomizing chamber. On its open side, this groove is closed by the porous filter surface that can be of flat design for this purpose and can therefore be produced very cost-effectively. The base component and the filter surface, which is preferably in the form of a membrane, can be joined together by gluing or welding.

It is regarded as being particularly advantageous when the aforementioned duct of the debubbling device comprises at least one curved or bent portion. Here, it is important that the porous filter surface be provided along this portion also. It has been found that such a curved portion promotes the escape of gas through the porous filter surface, presumably because most of the gas bubbles gather in the region of the inside bend of the curves and are conveyed at a reduced speed in this region. Preferably, several curved or bent portions are provided that are variably oriented relatively to each other so that the removal of the gas bubbles is possible at different orientations of the atomizer. Furthermore, the duct including curved portions that preferably interconnect linear portions produces a long path of flow for the liquid even in the case of a comparatively small component, so that gas bubbles can leave the intake channel through the porous filter surface over a comparatively long period of time.

As mentioned above, it is particularly advantageous when the liquid present in the liquid storage receptacle contains an active pharmaceutical ingredient and/or is a cosmetic product, more particularly a self-tanning lotion.

An atomizer of the invention can comprise flow meters both in the intake channel and in the return channel, in order to make it possible to precisely determine the amount of liquid that is atomized during a discharge process by taking the difference.

The atomizer of the invention is preferably in the form of a mobile device. For this purpose, it preferably comprises a battery or an accumulator. In one particular embodiment, the device comprises a user-exchangeable pack of consumables not requiring special tools and including at least the liquid-containing bladder. This pack of consumables can additionally include the battery. The comparatively expensive components such as the electronic control device, the pumping device, the debubbling device, and the atomizing device and optionally the accumulator can be components of a base unit, to which the outer pack of consumables can be coupled.

BRIEF DESCRIPTION OF THE DRAWINGS

Additional aspects and advantages of the invention are revealed in the claims and the following description of a preferred exemplary embodiment of the invention, which is explained with reference to the figures, in which:

DETAILED DESCRIPTION OF THE EXEMPLARY EMBODIMENT

Figure 1:
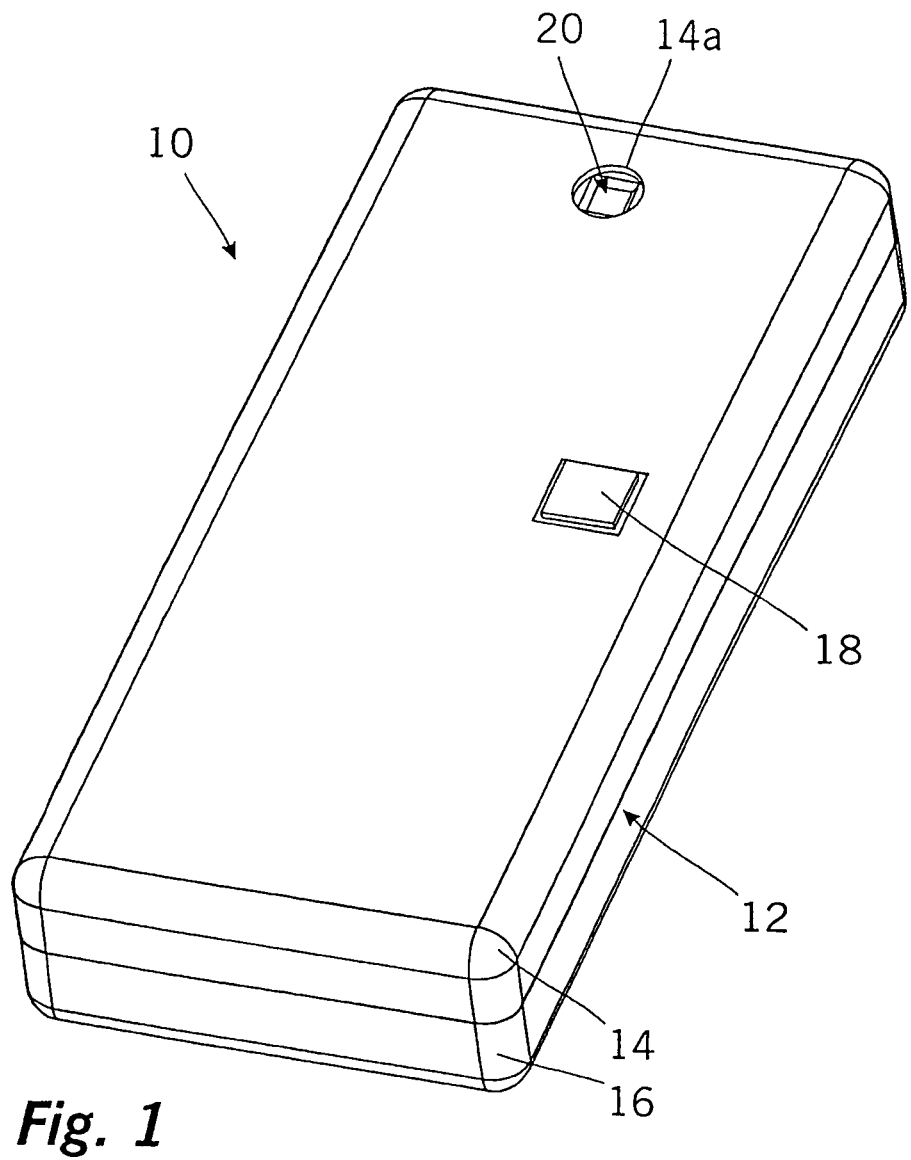
FIG. 1 is an overall view of an atomizer of the invention.

FIG. 1 is an overall view of an hand-held atomizer 10 of the invention. The atomizer 10 comprises a housing 12 that is approximately of the size of a cellular phone and that comprises two housing shells 14, 16. A recess 14a, behind which there is disposed an atomizing device 20 (explained in more detail below), is provided in the top housing shell 14. Furthermore, a control switch 18, by means of which the atomizer 10 can be activated, is provided at the front of the atomizer formed by the housing shell 14.

Figure 2:
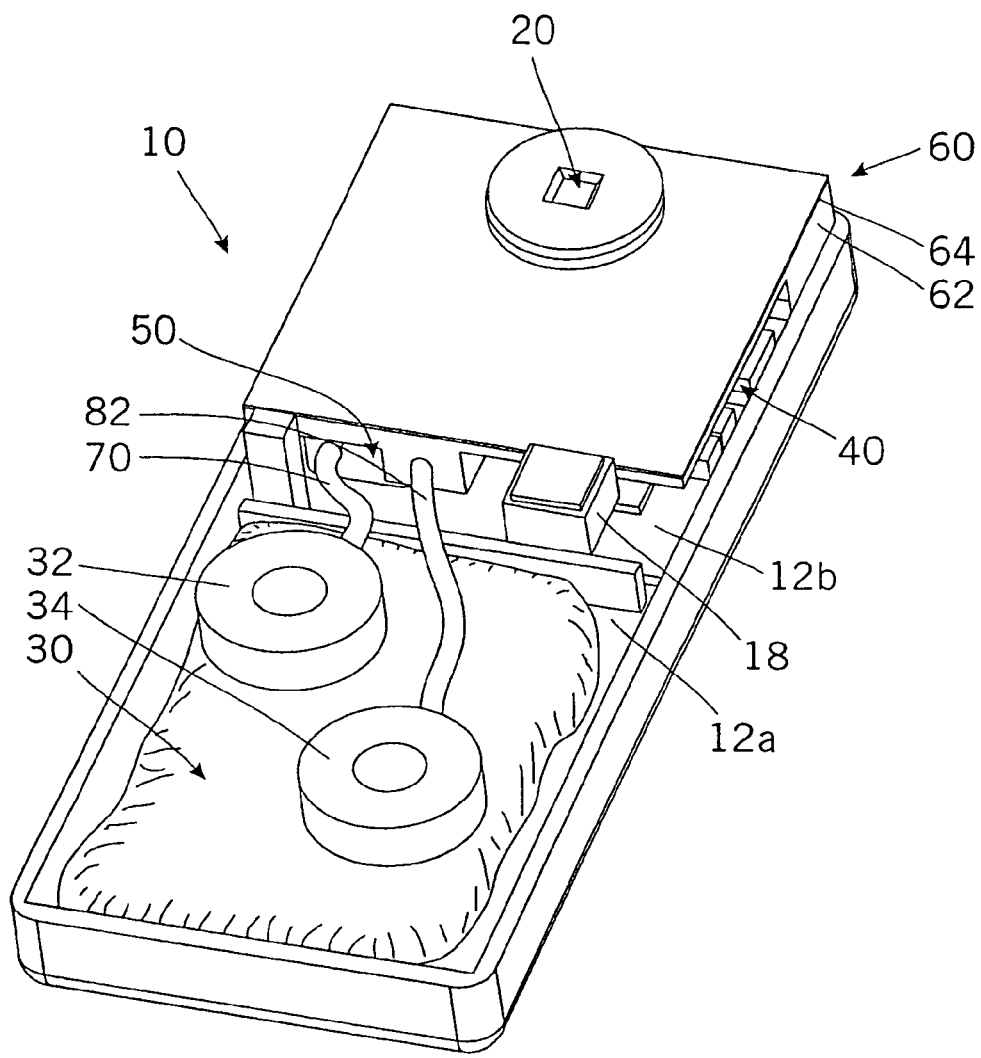
FIG. 2 shows the atomizer shown in FIG. 1 after removal of a housing shell.
Figures 3, 4:
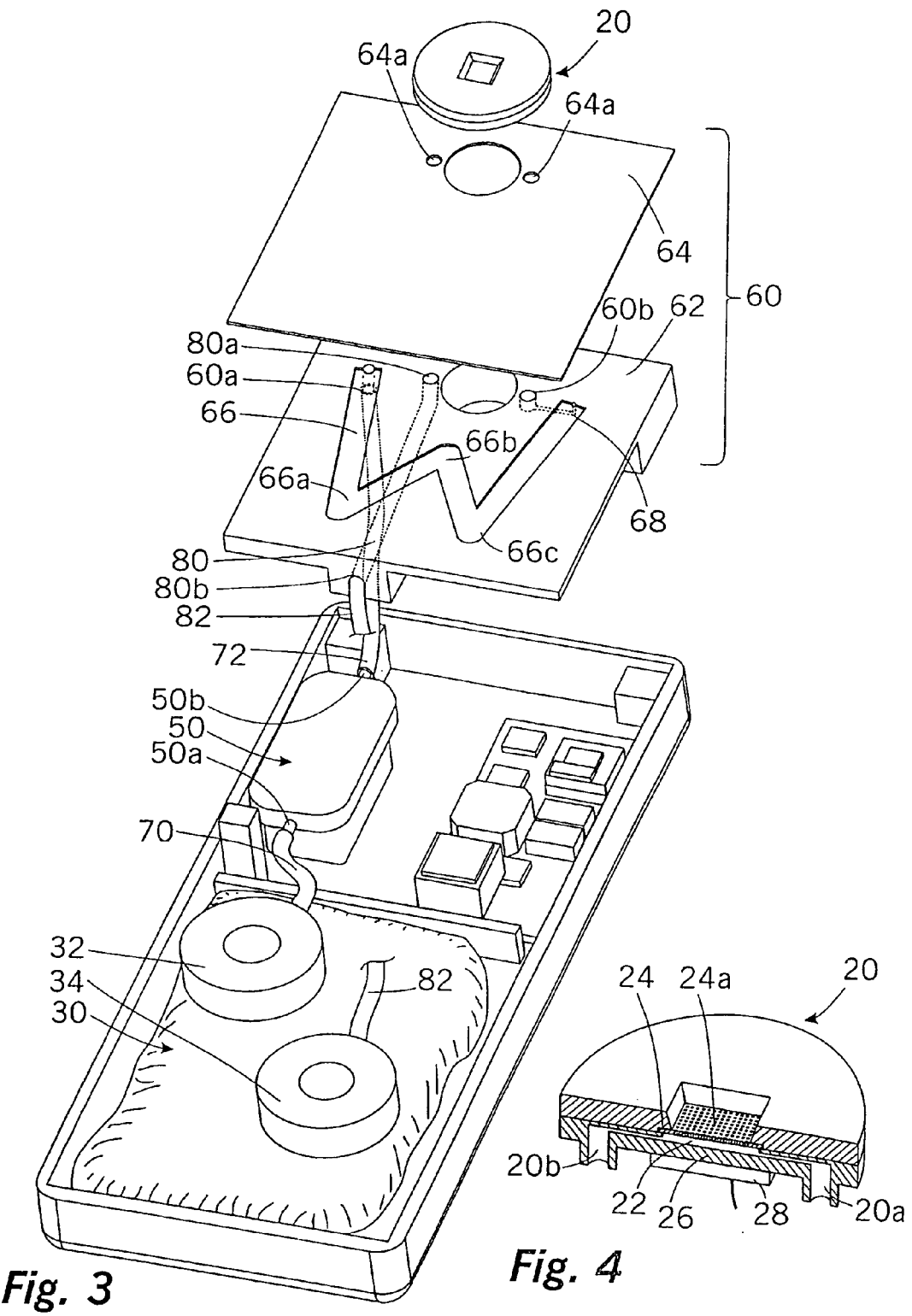
FIG. 3 is a partially exploded view of the atomizer shown in FIGS. 1 and 2.
FIG. 4 shows the atomizing device of the atomizer shown in FIGS. 1 to 3.

FIGS. 2 and 3 show the atomizer 10 in an open state, that is, after removal of the top housing shell 14. FIG. 3 shows some components in a position removed from the housing 12 to make it possible to identify all significant components.

Two distinct regions 12a, 12b are provided inside the housing 12. The region 12a contains a liquid storage receptacle 30 in the form of a liquid-containing bladder 30. Two openings (hidden in the figures), on each of which a coupling device 32, 34 is provided for connection to a flexible tube, are provided on the liquid-containing bladder 30.

The aforementioned control switch 18 and the aforementioned atomizing device 20 are disposed in the region 12b of the housing 12, Furthermore, a control device 40 and an accumulator (not shown) as an energy storage device are provided in this region. The region 12b additionally includes a piezoelectric pumping device 50 and a debubbling device 60.

The liquid-containing bladder 30 is connected to the atomizing device 20 in the following manner. The coupling device 32 is connected to the input side 50a of the pumping device 50 by means of a flexible tube 70. An additional flexible tube 72 connected to an inlet 60a of the debubbling device 60 is provided on the output side 50b of the pumping device 50. This inlet 60a adjoins a debubbling channel 66 that has been formed as a groove in a base component 62 of the debubbling device 60. As shown in FIG. 2, the base component 62 is closed in a liquid-tight manner in the assembled state of the atomizer 10 by means of a membrane 64, more particularly an acrylic copolymer-based membrane that has a hydrophobic top coating and that can be glued or welded to the base component 62 in the marginal regions of the groove. This membrane 64 is in the form of a porous membrane and serves the purpose of allowing gas bubbles to escape from the liquid flowing through the channel 66. At the opposite end of the channel 66, there is provided a throttle in the form of a bottle-neck region 68, the cross-sectional area of which is substantially smaller than that of the channel portion 66 upstream thereof. This bottle-neck region 68 adjoins an outlet orifice 60b of the debubbling device 60. The atomizing device 20 (shown on an enlarged scale in FIG. 4) is provided directly at this outlet 60b of the debubbling device 60, and through-holes 64a are provided in the membrane 64 to make this direct connection possible.

The atomizing device 20 comprises an atomizing chamber 22 located between a liquid inlet 20a and a liquid outlet 20b. On its side near the opening 14a of the top housing shell 14, this atomizing chamber 22 is delimited by a perforated plate 24 comprising a plurality of outlet orifices 24a. On its side remote from the perforated plate 24, the atomizing chamber 22 is provided with a wall 26, to which a piezoelectric vibrator 28 is attached, which is connected to the control device 40 by means of a cable (shown as a detail). Through-holes are provided in the base component 62 and in the membrane 64 for accommodating and wiring the piezoelectric vibrator 28.

The liquid outlet 20b is provided for the excess liquid flowing from the atomizing chamber 22. In the assembled state of the atomizer, this liquid outlet 20b communicates with the inlet 80a of a liquid channel 80 that passes through the base component 62 of the debubbling device 60 up to its outlet 80b without a debubbling function being assigned to this channel portion 80. A flexible tube 82 leading to the aforementioned second coupling device 34 of the liquid-containing bladder 30 is connected to the outlet 80b.

Thus the liquid-containing bladder 30 is connected to the atomizing device 20 by means of the channel portions 70, 72, 66. This is the intake channel. The return channel is formed by the channel portions 80 and 82.

The operation of the atomizer 10 is explained below.

For the purpose of discharging liquid from the liquid storage receptacle 30, the user activates the control switch 18. This activation of the control switch is registered by the electronic control device 40. In order to effect preparatory measures for a subsequent atomizing process, the electronic control device 40 activates the piezoelectrically operated micropump 50, initially alone. As a result, liquid is drawn in from the liquid storage receptacle 30 through the flexible tube 70 and is further transported through the flexible tube 72 to the debubbling device 60. Here, the liquid flows into the channel portion 66. Due to the pumping pressure built up at the output 50b of the pumping device 50 together with the throttling effect of the bottle-neck region 68, a comparatively high pressure builds up inside the channel portion 66. The positive pressure in the channel portion 66 relative to the environment preferably ranges from 100 mbar to 500 mbar.

This positive pressure is sufficient to dispel gas bubbles through the porous membrane 64 from the liquid drawn in, and the gas can then escape through gaps in the housing 12. The liquid delivered by the micropump 50 cannot escape through the porous membrane 64 at the aforementioned positive pressure. Thus the liquid entering the bottle-neck region 68 is largely free from gas bubbles. The W-shaped configuration of the channel portion 66, more particularly the three curves 66a, 66b, 66c, promote the process of removing bubbles, since the bubbles gather at the inside bend in the region of these curves 66a, 66b, 66c and are further conveyed comparatively slowly in this region. This gives sufficient time for the gas bubbles to escape through the porous membrane 64. The bottle-neck region 68 connected directly upstream of the atomizing device 20 leads to a significant reduction in the pressure of the liquid. The liquid largely free from gas bubbles therefore flows at a reduced pressure into the atomizing chamber 22. Since the vibrator 28 has not yet been activated at this point, the liquid flows from the inlet side 20a of the atomizing device 20 directly to the outlet side 20b of the atomizing device 20. The liquid pressure that is reduced by the bottle-neck region 68 to a positive pressure ranging from 0 mbar to 30 mbar and preferably from 2 mbar to 10 mbar, is initially not sufficient to force the liquid into the environment by way of the outlet orifices 24a. The outlet orifices 24a are thus not wetted. Instead, all the liquid delivered flows back into the liquid storage receptacle in the preparatory phase due to the low flow resistance in the channel portions 80, 82. In the preparatory phase, in which only the pumping device 50 but not the vibrator 28 is activated, the entire pumped volume of liquid is thus recirculated. Air that may still be present in the atomizing chamber 22 prior to activation of the control switch 18 is either forced out of the atomizing chamber 22 through the outlet orifices 24*a* when liquid flows into the atomizing chamber or forced through the channel portions 80, 82 into the liquid-containing bladder 30 to be removed from the liquid in the debubbling device 60 when the liquid is subsequently drawn in.

On termination of the preparatory phase, preferably after approximately one second, the vibrator 28 is also activated by the control device 40. As a result, the liquid present in the atomizing chamber 22 is caused to vibrate, which results in a discharge of liquid through the outlet orifices 24*a* in the form of extremely small droplets. Thus a fine liquid spray is dispensed through the orifice 14*a* in the top housing shell 14, and this liquid spray can be inhaled, for example as a medicine, or dispensed onto the skin in the form of a cosmetic deposit, when the appropriate liquid is used.

Once the vibrator 28 has been switched into operation, a portion, preferably half or a major portion of the pumped volume of liquid delivered by the pumping device 50 to the atomizing device 20 is dispensed through the outlet orifices 24*a*. There still remains a significant portion of the liquid delivered by the pumping device 50, which portion is recirculated to the liquid-containing bladder 30 through the channel portions 80, 82. This ensures that any air that may have inadvertently entered the atomizing chamber 22 is reliably removed therefrom. At the same time, the fact that the pumped volumetric flow rate is greater than the discharged volumetric flow rate reliably ensures that a sufficient amount of liquid is present in the atomizing chamber 22 at all times.

The invention claimed is:

1. An atomizer for atomizing liquids, comprising:

a liquid storage receptacle in the form of a dimensionally flexible liquid-containing bladder, an atomizing device having an atomizing chamber that communicates with the ambient atmosphere via a plurality of outlet orifices, the atomizing device having a liquid inlet and a liquid outlet each communicating with the atomizing chamber, and further having a vibrator which vibrates liquid present in the atomizing chamber to atomize same, the atomizing chamber being delimited on one side by the outlet orifices and on an opposite side by a vibrating wall which is vibrated by the vibrator, an intake channel fluidly interconnecting said liquid storage receptacle to the liquid inlet of the atomizing device, a debubbling device located in the intake channel, said debubbling device having a channel portion through which liquid flows on its way to said atomizing chamber and which channel portion is partly delimited by a filter surface, wherein said channel portion:

is formed by a groove in a base component of the atomizer, the groove being closed by said filter surface, the filter surface being flat and porous and positioned on said base component, or has at least two straight portions interconnected by at least one curved portion;

an electrically actuated pumping device provided in said intake channel for delivering liquid from said liquid storage receptacle to said atomizing chamber, an electronic control device electrically controlling said pumping device and said vibrator, said atomizing device and said pumping device being configured or being controlled by said control device such that during atomization a pumped volumetric flow rate of the liquid transported by said pumping device is greater than a discharged volumetric flow rate through said outlet orifices as achieved by said atomizing device, and a return channel distinct from said intake channel, the return channel fluidly interconnecting the liquid storage receptacle to the liquid outlet of the atomizing device, the return channel draining liquid from said atomizing chamber into said liquid storage receptacle.

2. The atomizer as defined in claim 1, wherein the pumped volumetric flow rate during atomization is greater than the discharged volumetric flow rate by at least 20%.

3. The atomizer as defined in claim 1, wherein said control device is adapted to first activate only said pumping device in a preparatory phase prior to commencement of a discharging operation, and second to additionally activate said vibrator on termination of the preparatory phase.

4. The atomizer as defined in claim 3, wherein said pumping device is configured or is controlled by said control device in such a manner, and said outlet orifices of said atomizing device are constructed in such a manner, that the pressure achieved in the atomizing chamber in the preparatory phase is not sufficient to force liquid through said outlet orifices.

5. The. atomizer as defined in claim 1, wherein the debubbling device is provided between said pumping device and said atomizing chamber.

6. The atomizer as defined in claim 1, wherein said pumping device is configured or is controlled by said control device in such a manner, and said debubbling device is configured in such a manner, that the pressure established in said debubbling device suffices to force gas through the filter surface but is not sufficient to force liquid through said filter surface.

7. The atomizer as defined in claim 1, wherein the liquid present in said liquid storage receptacle contains a pharmaceutically active substance or is a cosmetic product.

8. An atomizer for atomizing pharmaceutical or cosmetic liquids, said atomizer comprising:

a liquid storage receptacle;

an atomizing device defining an atomizing chamber, a plurality of outlet orifices in fluid communication with said atomizing chamber and the atmosphere, a liquid inlet and a liquid outlet each in fluid communication with said atomizing chamber, and a vibrating device disposed closely adjacent said atomizing chamber which when actuated vibrates liquid located within said atomizing chamber in order to atomize same;

an intake channel disposed to provide fluid communication between said liquid storage receptacle and said liquid inlet of said atomizing device to place said atomizing chamber in fluid communication with said liquid storage receptacle and allow delivery of fluid therein to said atomizing chamber;

an electrically-actuated pumping device disposed to deliver liquid from said liquid storage receptacle to said atomizing chamber via said intake channel;

an electronic control device electrically controlling and electrically connected to said pumping device and said vibrating device; a return channel separate and distinct from said intake channel, said return channel fluidly interconnecting said liquid storage receptacle to said liquid outlet of said atomizing device to drain liquid from said atomizing chamber and recirculate liquid therein back into said liquid storage receptacle;

a housing in which said liquid storage receptacle, said atomizing device, said intake channel, said pumping device, said control device and said return channel are disposed; and a debubbling device disposed between said pumping device and said atomizing chamber in said housing, said debubbling device including a base component and a porous membrane disposed in opposed relation with one another within said housing, said base component defining therein a debubbling groove closed on a side thereof by said membrane, said debubbling groove being in fluid communication with and forming part of said intake channel and having two substantially straight portions and a curved portion disposed between said two substantially straight portions.

9. The atomizer of claim 8, wherein said atomizing chamber is disposed between said liquid inlet and said liquid outlet.

10. The atomizer of claim 8, wherein said atomizing device includes a perforated plate defining therein said outlet orifices and a vibrating wall disposed in juxtaposed and facing relation with said perforated plate, said vibrating device being attached to said vibrating wall and vibrating same when actuated by said control device.

11. The atomizer of claim 8, wherein said control device electrically actuates only said pumping device in a preparatory phase prior to commencement of a discharging operation of said atomizer, said atomizer in the preparatory phase being configured to deliver liquid from said liquid storage receptacle to said atomizing chamber via said intake channel and then to recirculate the liquid to said liquid storage receptacle via said return channel, said pumping device achieving a pressure in said atomizing chamber in the preparatory phase which is insufficient to force liquid through said outlet orifices.

12. The atomizer of claim 11, wherein said control device electrically actuates both said pumping device and said vibrating device upon termination of the preparatory phase to commence the discharging operation, said atomizer during the discharging operation dispensing liquid through said outlet orifices, wherein a pumped volumetric flow rate of liquid transported by said pumping device during the discharging operation is greater than a discharged volumetric flow rate of liquid dispensed through said outlet orifices.

* * * * *